(12) United States Patent
Gulachenski et al.

(10) Patent No.: US 9,089,405 B1
(45) Date of Patent: Jul. 28, 2015

(54) THREE-DIMENSIONAL COMPLEX COIL

(75) Inventors: Joseph Gulachenski, Trabuco Canyon, CA (US); Heath Bowman, Trabuco Canyon, CA (US); Cathy Lei, Chino Hills, CA (US); Leticia Hurtado, Tustin, CA (US)

(73) Assignee: MicroVention, Inc., Tustin, CA (US)

( * ) Notice: Subject to any disclaimer, the term of this patent is extended or adjusted under 35 U.S.C. 154(b) by 1174 days.

(21) Appl. No.: 12/559,427

(22) Filed: Sep. 14, 2009

Related U.S. Application Data (60) Provisional application No. 61/096,740, filed on Sep. 12, 2008.

(51) Int. Cl.
*A61F 2/01* (2006.01)
*A61F 2/95* (2013.01)

(52) U.S. Cl.
CPC .. *A61F 2/013* (2013.01); *A61F 2/95* (2013.01)

(58) Field of Classification Search
CPC ............. A61B 17/12022; A61B 17/12113; A61B 17/12145; A61B 2017/00526; A61B 2017/00867; A61B 17/1215; A61B 17/1214

USPC ............. 606/200, 198, 158, 151, 157, 194; 140/102.5, 103, 102; 623/1.15, 1.1, 623/1.18, 1.2, 1.21, 1.22

See application file for complete search history.

(56) References Cited

U.S. PATENT DOCUMENTS

| | | | |
|---|---|---|---|
| 5,639,277 A * | 6/1997 | Mariant et al. | 606/191 |
| 5,749,891 A * | 5/1998 | Ken et al. | 606/200 |
| 6,322,576 B1 * | 11/2001 | Wallace et al. | 606/191 |
| 2003/0018356 A1* | 1/2003 | Schaefer et al. | 606/200 |
| 2005/0192618 A1* | 9/2005 | Porter | 606/200 |
| 2007/0175536 A1* | 8/2007 | Monetti et al. | 140/102.5 |

* cited by examiner

*Primary Examiner* — Katrina Stransky
*Assistant Examiner* — Sidharth Kapoor
(74) *Attorney, Agent, or Firm* — Inskeep IP Group, Inc.

(57) ABSTRACT

A complex coil configured such that in a relaxed, minimum energy state configuration loops are formed having various orientations relative to each other. The complex coil provide improved thrombus formation and reduced rotation or tumbling once implanted. The complex coil is formed of a material that may be deformed for purposes of placing the complex coil into a catheter and returns to a complex shape that includes said loops once deployed.

24 Claims, 13 Drawing Sheets

THREE-DIMENSIONAL COMPLEX COIL

RELATED APPLICATIONS

This application claims priority to U.S. Provisional Application Ser. No. 61/096,740 filed Sep. 12, 2008, entitled Three-Dimensional Complex Coil, which is hereby incorporated herein by reference.

FIELD OF THE INVENTION

This invention relates generally to the field of vascular occlusion devices and methods. More specifically, it relates to an apparatus and method for embolizing a targeted site such as an aneurysm in the blood vessel.

BACKGROUND OF THE INVENTION

The prior art contemplates a number of methods and devices for treating an aneurysm using three-dimensional (3-D) shaped coils, sometimes referred to as "complex coils." For example, U.S. Pat. No. 5,766,219 to Horton, the contents of which are incorporated by reference, shows a hollow coil structure. U.S. Pat. No. 5,382,259 to Phelps and U.S. Pat. No. 4,994,069 to Ritchart, the contents of which are incorporated by reference, show other 3-D coil designs. U.S. Pat. No. 6,635,069 to Teoh, the contents of which are incorporated by reference, teaches a series of non-overlapping loops. U.S. Pat. No. 6,860,893 to Wallace, the contents of which are incorporated by reference, shows alternative complex coils. U.S. Pat. No. 6,638,291 to Ferrera, the contents of which are incorporated by reference, shows a device similar to Teoh's and Wallace's except that a J-shaped proximal segment extends away from the complex portion of the device.

The following patents and published patent applications provide further background and are also incorporated herein by reference: U.S. Pat. No. 6,010,498 to Guglielmi; U.S. Pat. No. 6,478,773 to Gandhi; U.S. Pat. No. 5,957,948 to Mariant; U.S. Pat. No. 5,911,731 to Pham; U.S. Pat. No. 4,957,501 to Lahille; and U.S. Publication Nos. 2005/0192618 to Porter, 2005/0192621; to Wallace; and 2002/0107534 to Schaefer;

There is, however an ongoing need to provide more advanced and improved complex coils that exhibit greater stability after deployment and increased efficacy for treating aneurysms.

SUMMARY OF THE INVENTION

One aspect of the present invention provides improved devices and methods for treating an aneurysm. Another aspect of the present invention pertains to a device that includes a strand of material that self-forms into a compound shaped series of loops oriented predominately longitudinally about and through a central axis when the device is in a relaxed or low energy state configuration.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figures 1, 2:
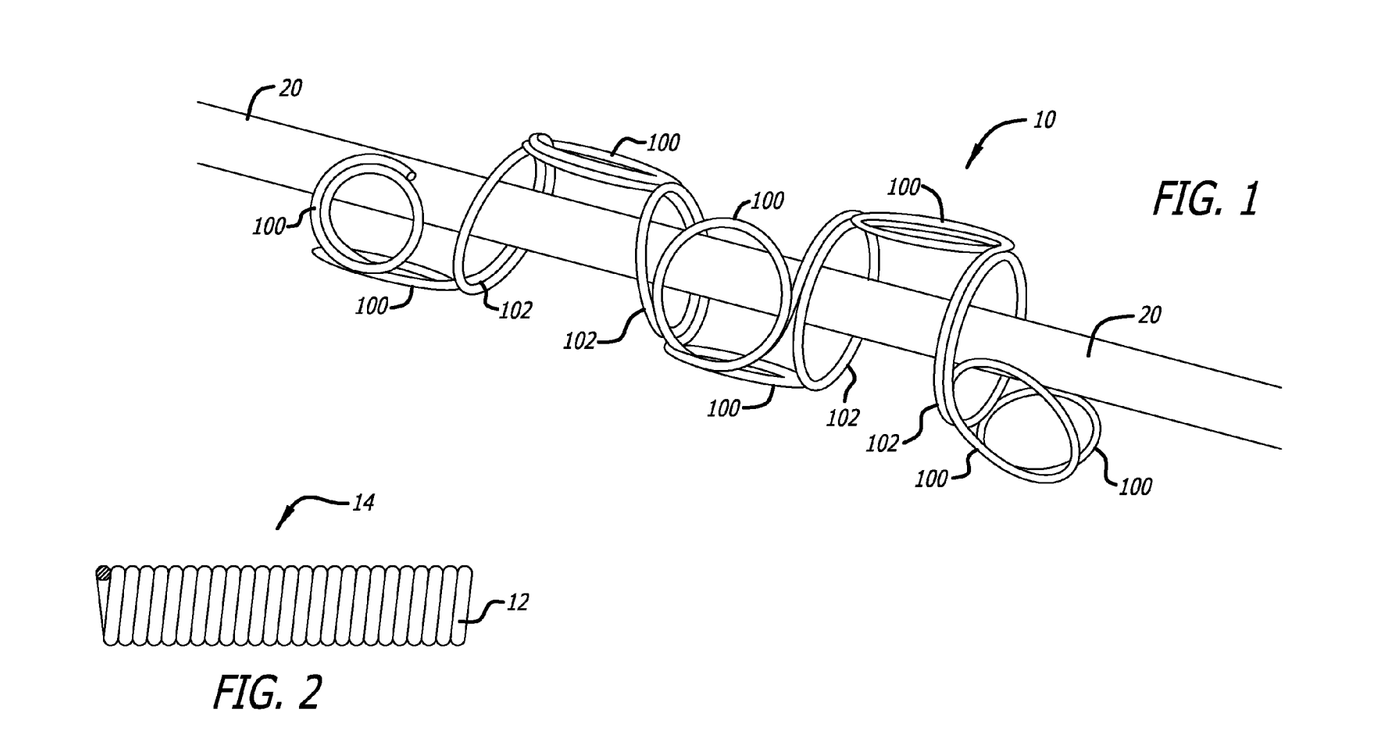
FIG. 1 is a perspective view of an embodiment of a device according to the present invention.
FIG. 2 is a perspective view of a portion of a microcoil employed to form a device according to the present invention.

Referring first to FIGS. 1 and 2, a microcoil vaso-occlusive device 10, in accordance with a preferred embodiment of the invention is shown. For the sake of clarity and in order to provide greater perspective to the FIG. 1, the device 10 of FIG. 1 is shown with a central axis 20 that appears as a dowel, i.e. appears exaggerated in size. It is to be understood that central axis 20 is merely an axis and is not a physical component of the device 10. The device 10 comprises a suitable length of wire 12 formed into the primary configuration of a helical microcoil 14. Suitable materials for the microcoil 14 include platinum, rhodium, palladium, rhenium, tungsten, gold, silver, tantalum, and various alloys of these metals. Various surgical grade stainless steels may also be used. Preferred materials include the platinum/tungsten alloy known as Platinum 479 (92% Pt, 8% W, available from Sigmund Cohn, of Mount Vernon, N.Y.) and titanium/nickel alloys (such as the titanium/nickel alloy known as "Nitinol"). Another material that may be advantageous is a bimetallic wire comprising a highly elastic metal with a highly radiopaque metal. Such a bimetallic wire would also be resistant to permanent deformation. An example of such a bimetallic wire is a product comprising a Nitinol outer layer and an inner core of pure reference grade platinum, available from Sigmund Cohn, of Mount Vernon, N.Y., and Anomet Products, of Shrewsbury, Mass.

The wire 12 employed to form microcoil 14 has a diameter in the range of 0.001 to 0.005 inches. The microcoil 14 has a diameter that is typically in the range of about 0.008 to 0.016 inches. The axial length of the microcoil 14 may be anywhere from about 5 to 100 cm.

The primary winding of the microcoil 14 is applied under tension. The amount of tension and the pitch of the primary winding determine the stiffness of the microcoil 14. These parameters can be varied along the length of the microcoil 14 to form a microcoil having different degrees of stiffness along its length, which may be advantageous in certain applications.

The primary microcoil 14 is formed into the secondary configuration by heat treatment, as is well known in the art. For example, the annealed primary coil may be initially placed into the secondary configuration by winding or wrapping the microcoil 14 around a suitably shaped and sized mandrel, or fixture, of refractory material, and then subjecting the microcoil wrapped mandrel to an annealing temperature for a specified period of time. For example, an annealing temperature of about 500 degrees Celsius to about 1000 degrees Celsius, is maintained for about 30 to 90 minutes, then cooled to room temperature and ultrasonically cleaned. The resultant secondary configuration is thereby made permanent and becomes the relaxed or minimum energy state configuration of the microcoil 14.

Figure 3:
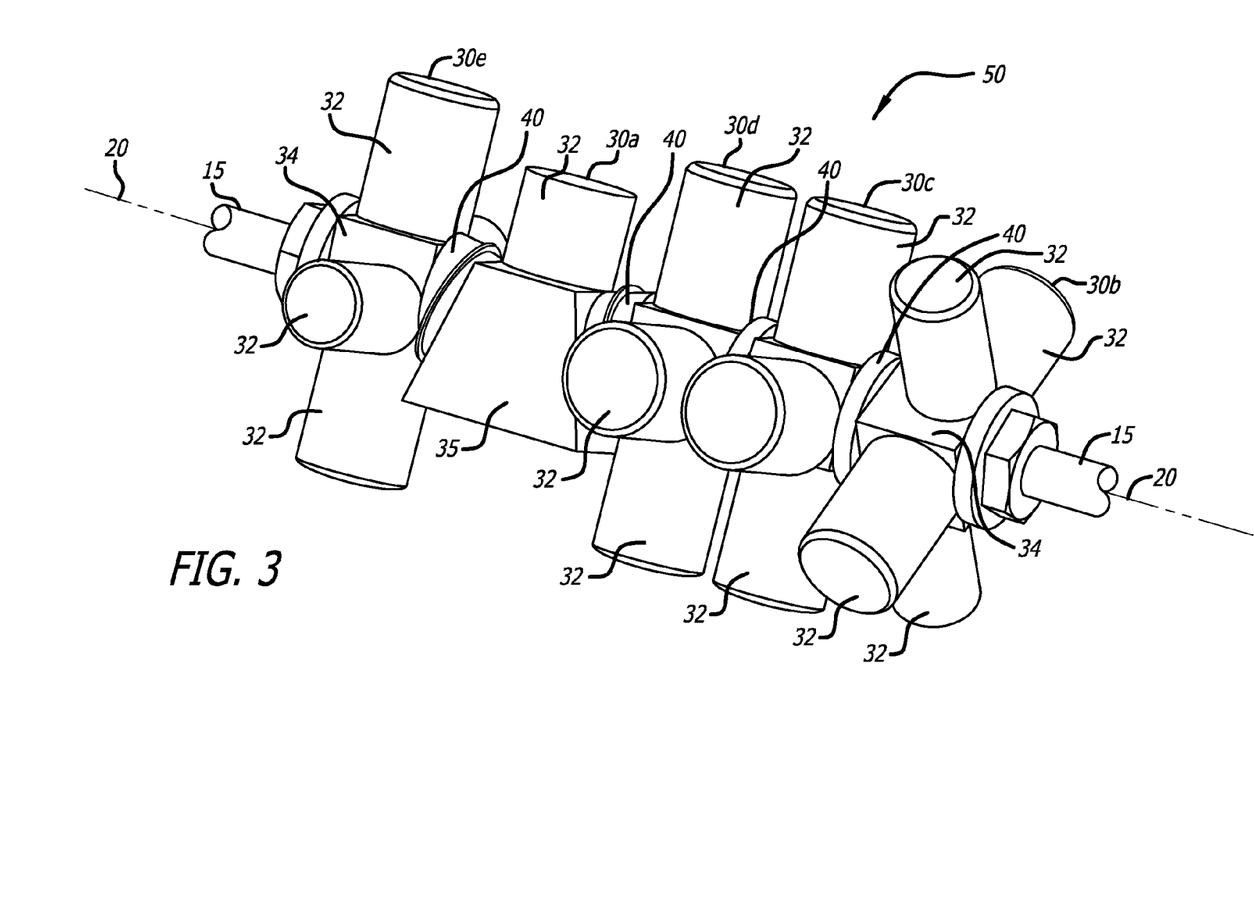
FIG. 3 is a perspective view of an embodiment of a mandrel employed to fabricate a device according to the present invention.
Figure 10:
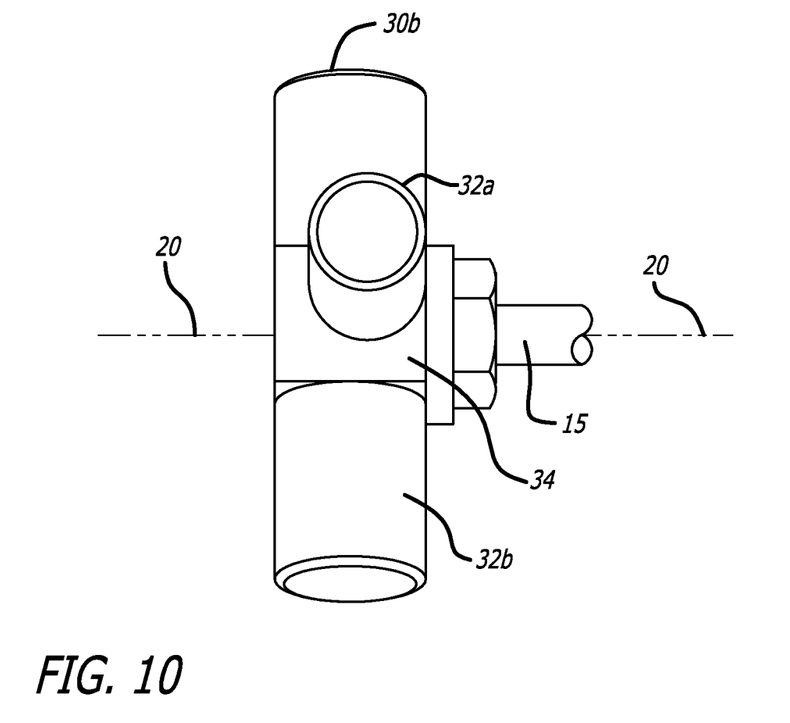
FIG. 10 is a perspective view of an embodiment of a mandrel employed to fabricate a device according to the present invention.

FIG. 3 shows a mandrel or heat treatment fixture 50 used in the manufacture of the preferred embodiment of the invention. The mandrel 50 comprises a shaft 15 defining a central axis 20 through the mandrel. The exemplary mandrel 50 shown in FIG. 3 further employs assemblies 30a-e separated by disks 40. As illustrated, the assemblies 30a-e may have attached thereto pins 32. The pins 32 may be formed in various diameters and cross-sectional shapes, such as circular, ovular, triangular, or rectangular shapes. For example, the pins 32 may have a diameter of about 3 mm to 25 mm. Furthermore, the pins 32 may be attached to the assembly body 34 in either a regular, centered configuration relative to the assembly body 34, or the pins 32 may be attached in an irregular, off-centered configuration relative to the assembly body 34. For example, as best illustrated in FIG. 10, an assembly 30b comprises a pin 32a attached to the assembly body 34 in an irregular configuration, and a pin 32b attached to the assembly body 34 in a regular configuration. The regular and irregular configurations of the pins 32 relative to the assembly bodies 34 are employed, at least in part, in order that adjacent loops may be tangentially-interconnected to one another. Stated alternatively, the regular and irregular configurations of the pins 32 relative to the assembly bodies 34 may facilitate interconnecting adjacent loops such that the adjacent loops connect with one another at a shared or common approximate tangent.

The assembly bodies 34 may also be configured in various sizes and shapes, for example, an assembly body 35 of an assembly 30a, as seen in FIG. 3, is formed in the general shape of a trapezoid. The assembly bodies 34 may be formed in numerous other shapes such as rectangles, triangles, spheres, or parallelograms. As illustrated in FIG. 3, the assembly body 34 and the pins 32 of the assembly 30a-e may be configured so as to form a cross or plus sign when placed over the shaft 15 and viewed along the central axis 20. As will also be noted from FIG. 3, the assemblies 30a-e may be mounted over the shaft 15 at different radial orientations relative to the other assemblies 30a-e mounted on the shaft 15. For example, the assembly 30b is askew from the general orientation of the assemblies 30a and 30c-e.

To form the secondary configuration of the microcoil 14, the microcoil 14 is first anchored to an end of the mandrel 50. The microcoil 14 is then wrapped around either a first disk 40 or a first pin 32 to form loops 102 or 100, respectively, see FIG. 1. Upon completion of a first loop, the microcoil 14 may, for example, be brought to a second pin 32, if fabrication began on a first pin 32, or to a first disk 40, if fabrication began on a first pin 32, or to a first disk 40, if fabrication began on a pin 32. In a preferred embodiment, the microcoil 14 does not transition from one disk 40 to another disk 40 without wrapping around at least one pin 32 there between. The microcoil 14 is wrapped around the second location to form a second loop and the process is repeated until the desired device 10 has been formed. During the secondary winding process, the primary coil 14 is kept under tension. The amount of tension is adjusted to control the structural characteristics of the secondary configuration.

The number of revolutions or turns that the primary coil 14 is wound around the disks 40 or the pins 32 will depend on the configuration of the loops 100 and 102 of the device 10. For example, if a loop 102 is interposed between two loops 100 that are connected to the loop 102 at approximately 180 degrees apart, the loop 102 may be wound 1.5 revolutions around the disk 40 from which the loop 102 is formed. The number of revolutions that the primary coil 14 is wound around the disks 40 or the pins 32 may also be adjusted in order to control structural characteristics of the secondary structure. The direction of the revolutions or turns that the primary coil 14 is wound around the disks 40 or the pins 32 so as to minimize the space or length of coil 14 occurring between adjacent connected loops. For example, the direction of the revolutions may alternate between adjacent connected loops.

Figure 4A:
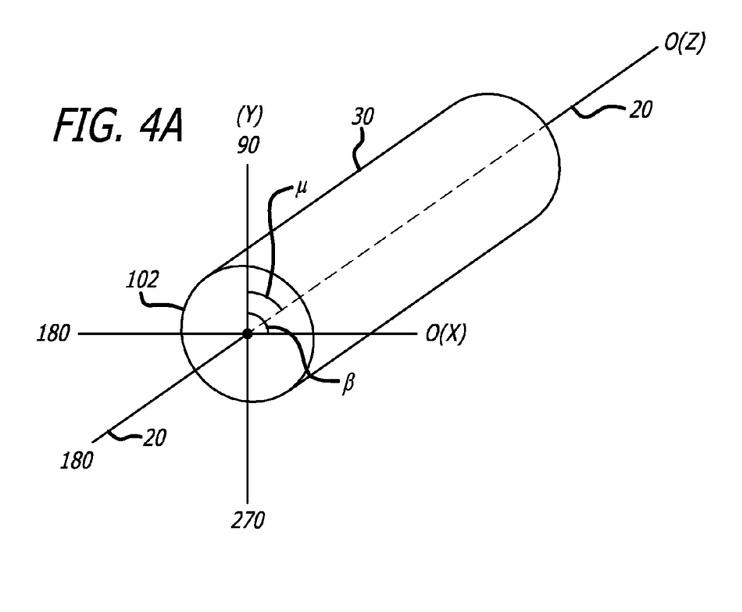
FIG. 4A-4B are illustrations of a frame of reference in which a device according to the present invention may be described.
Figure 4B:
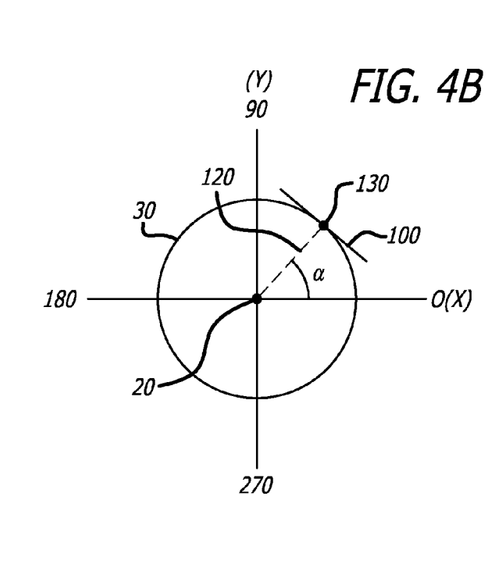

In order to facilitate the detailed description of the orientation and position of the various loops that comprise certain embodiments of the device 10, FIGS. 4A and 4B illustrate a general frame of reference. Devices according to the present invention may be conceptualized, for example, as employing a series of interconnected loops that are either oriented in a planar manner around the circumference 30 of the central axis 20 or oriented so as to intersect the central axis 20. As described above, loops are either formed by wrapping microcoil 14 around a disk 40, forming loops 102, or a pin 32, forming loops 100. Regarding the loops 100, loops that are oriented around the circumference 30 of the central axis 20, viewed in cross-section, these loops create a plane that forms a tangent 130 to the circumference 30. A radius 120 is formed by connecting the central axis 20 and the tangent 130. A tangent angle α (alpha) is determined by measuring the angle of the radius 120 from zero degrees in an X, Y plane. The loops 100 that are oriented around the circumference 30 of the central axis 20 are formed, for example, by wrapping of the microcoil 14 around the pins 32 of the assembly 32a-e, see FIG. 3. As will be noted, the length of radius 120 may vary such that while a first and second loop 100 of device 10 may have equal tangent angles α they may be positioned at different points along the length of radius 120.

With respect to those loops 102 that intersect the central axis 20, such loops 102 are formed by wrapping the microcoil 14 around the disks 40. The orientation of loops 102 intersecting the central axis 20 are described in terms of the loop's 102 Z,Y offset or intersecting angle μ (mu), as illustrated in FIG. 4A. Additionally, in certain configurations it may also be necessary to refer to the loop's 102 X,Y angle of rotation or rotational angle β (beta). For example, a loop 102 that intersects the central axis 20 substantially perpendicular to central axis 20 would have a intersecting angle μ of zero degrees and a rotational angle β of zero degrees.

The following provides detailed descriptions of the configurations of various example devices 10 according to certain embodiments of the present invention. Example 1 will be described in the form of a table, as well as textually with respect to the above described reference scheme. Various other examples will be described only in the form of a table according to the same principles and procedure describe with respect to Example 1.

With respect to Tables 1-4, loop diameters are provided for each of the loops forming the exemplary devices of Examples 1-4. The loop diameters are referenced to a "nominal" diameter which is determined by the size of the vascular irregularity or aneurysm intended for treatment. Each loop diameter is referenced as either equal to the nominal diameter or a variation from the nominal diameter. For example, if the nominal diameter is equal to 6 mm, each loop characterized as nominal has a diameter of 6 mm. A loop characterized as "-2" has a 4 mm diameter.

Example 1

TABLE 1

DESCRIPTION OF EXAMPLE 1

| Loop No. | Loop Diameter (mm) | Assembly No. | Tangent Angle (α) (Deg.) | Disk No. | Intersecting Angle (μ) (Deg) | Rotational Angle (β) (Deg) |
|---|---|---|---|---|---|---|
| 201 | -2 | 1 | 0 | | | |
| 202 | -1 | 1 | 270 | | | |
| 203 | Nominal | | | 1 | 90 | 0 |
| 204 | -1 | 2 | 135 | | | |
| 205 | Nominal | | | 2 | 90 | 0 |
| 206 | -1 | 3 | 225 | | | |
| 207 | -1 | 3 | 315 | | | |
| 208 | -1/2 | | | 3 | 75 | 45 |
| 209 | -1 | 4 | 135 | | | |
| 210 | -1/2 | | | 4 | 345 | 45 |
| 211 | -1 | 5 | 315 | | | |
| 212 | -2 | 5 | 225 | | | |

Figure 5:
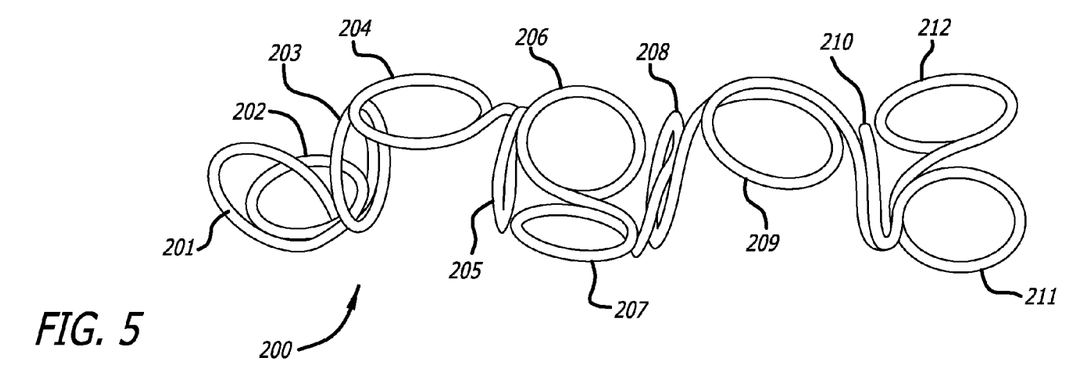
FIG. 5 is a perspective view of a wire model of an embodiment of a device according to the present invention.
Figure 6:
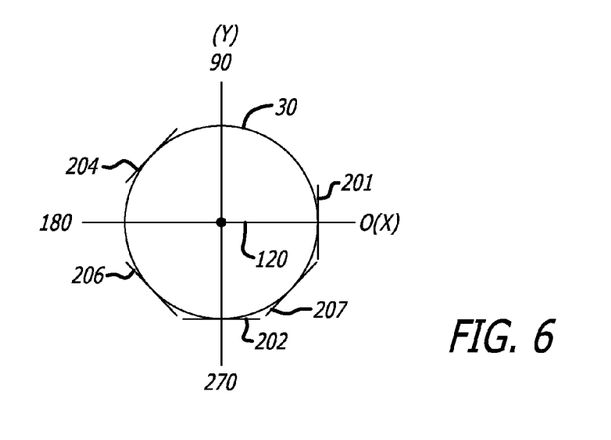
FIG. 6 is an illustration of a frame of reference in which a device according to the present invention may be described.
Figure 7A:
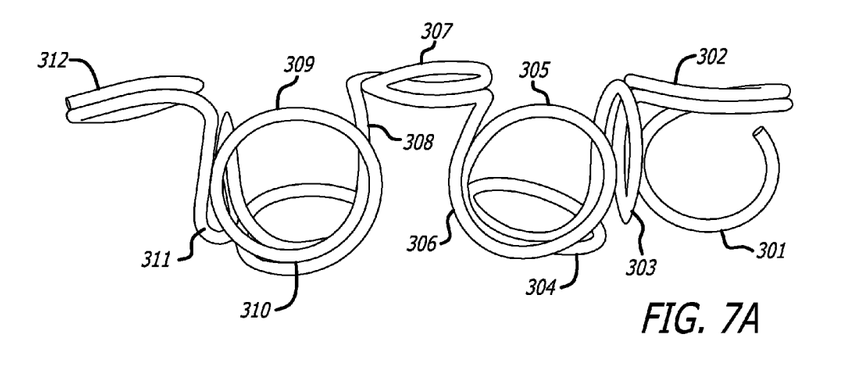
FIGS. 7A-7D are perspective views of a wire model of an embodiment of a device according to the present invention.
Figure 7B:
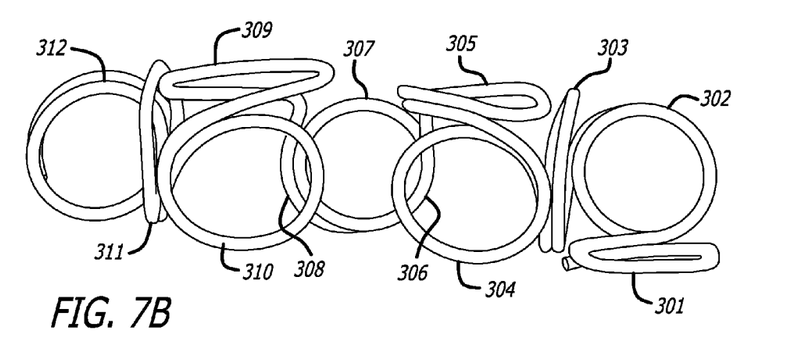
Figure 7C:
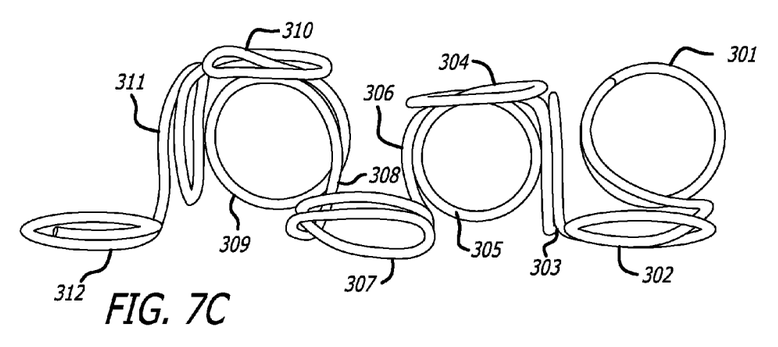
Figure 7D:
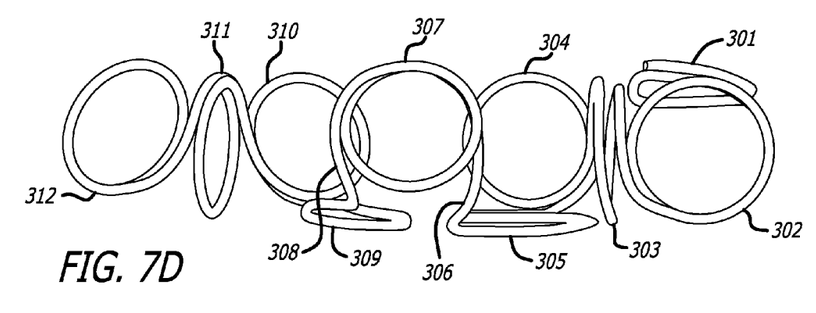
Figure 8A:
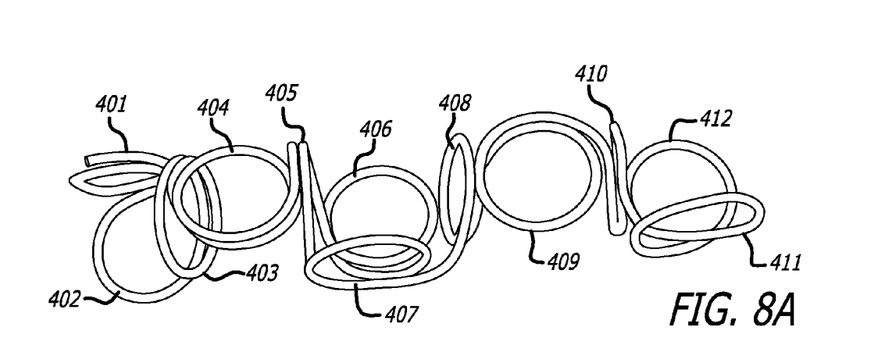
FIGS. 8A-8D are perspective views of a wire model of an embodiment of a device according to the present invention.
Figure 8B:
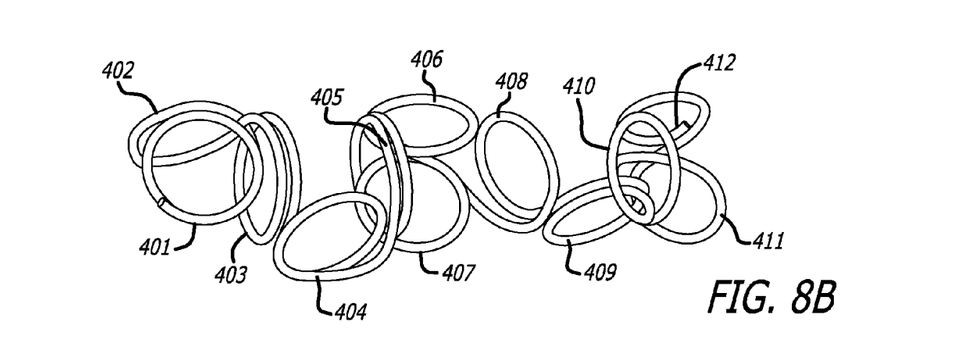
Figure 8C:
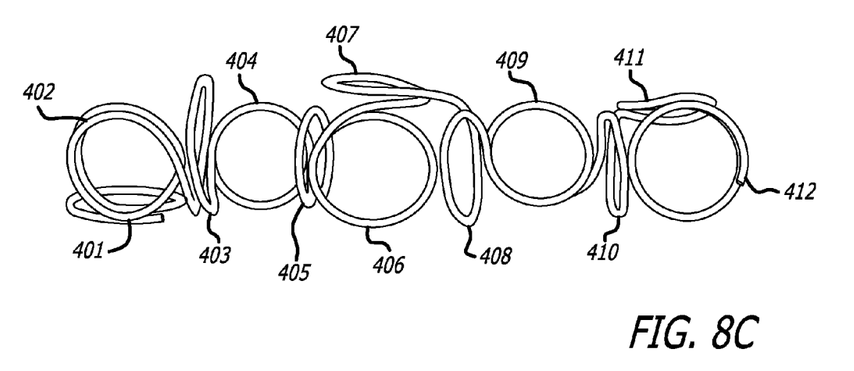
Figure 8D:
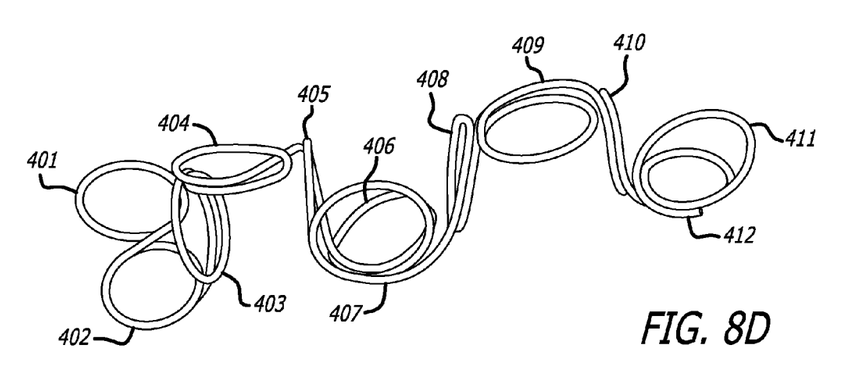
Figure 9A:
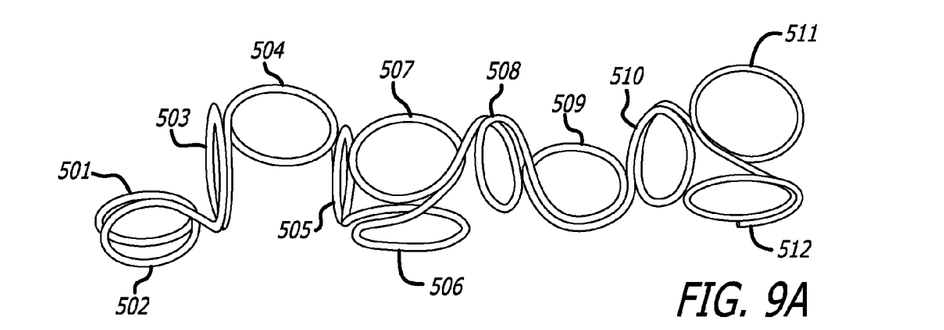
FIGS. 9A-9D are perspective views of a wire model of an embodiment of a device according to the present invention.
Figure 9B:
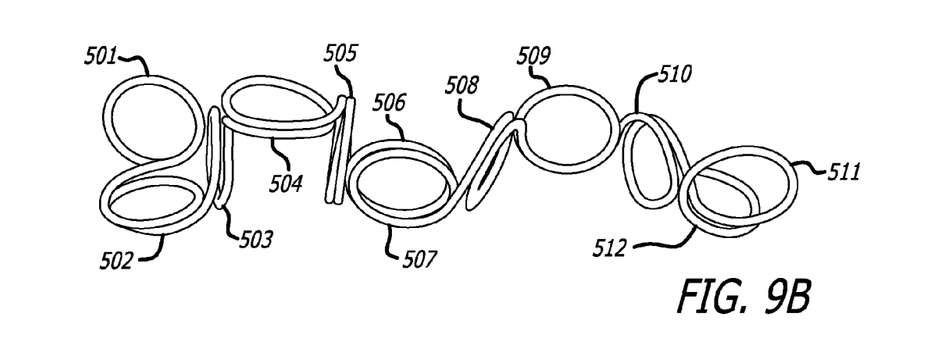
Figure 9C:
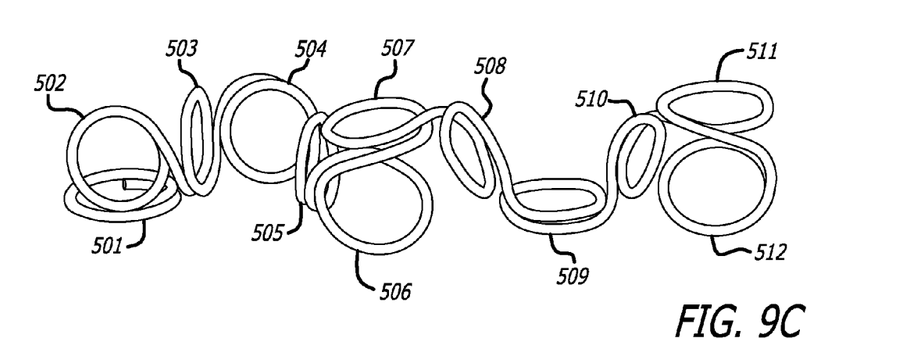
Figure 9D:
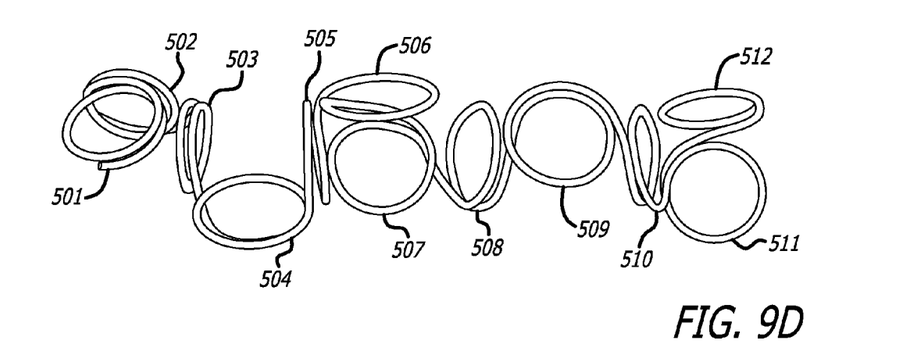
Figure 9E:
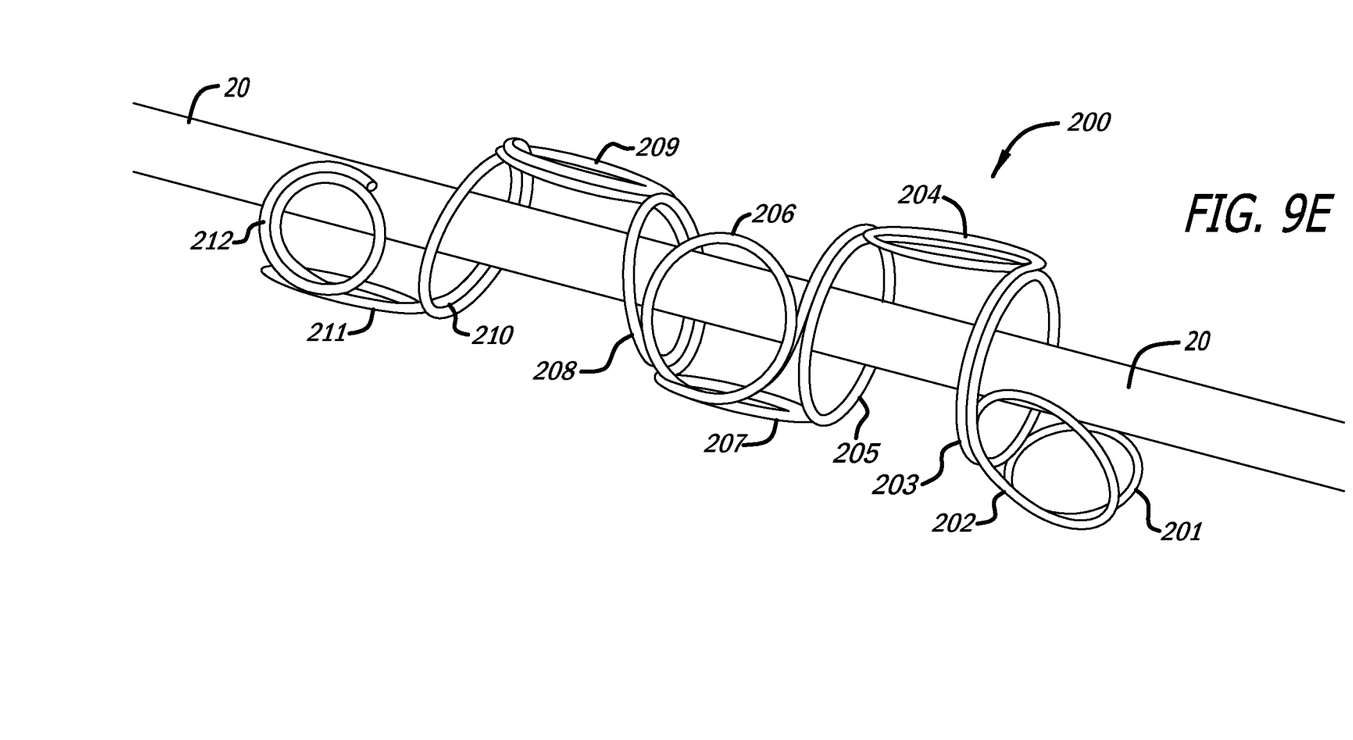
FIG. 9E is a perspective view of an embodiment of a device according to the present invention.

With reference to FIGS. 5 and 9E, device 200 includes loops 201-212. Loops 201-212 connect to one another in the same order as they are numbered. As noted in TABLE 1 and illustrated in FIG. 6, The loop 201, the first loop of device 200, is oriented so as to have a tangent angle α of zero (0) degrees with the device 200 oriented such that loop 201 is nearest the viewer's eye when the device is viewed along the central axis 20. That is to say, the first loop will serve to define the start position for reference to the remaining loops 202-212. It should also become apparent based on the above description of devices according to the present invention, that each loop is either characterized as a loop 100 or a loop 102. With respect to loops 100, for the sake of description, loops 100 will be referenced according to the common or shared assemblies 30 from which the loop is formed, as well as according to each loop's 100 tangent angle α. Assemblies 30 are referenced starting from the first loop 100. For example, loop 201 and 202 would have been formed from the same assembly and such assembly would be the first assembly, because it coincides with loop 201, see TABLE 1. Loops 102 may optionally be placed between the loops 100. As with reference to the assemblies 30 and the loops 100, reference to the disks from which the loops 102 are formed begin with the first loop 102 occurring in the device.

With specific reference to TABLE 1 and FIGS. 4A through 6 and 9E, the configuration of device 200 will be described. Loop 201 is oriented so as to have a tangent angle α of about zero degrees and defines the first assembly. Loop 202 is also within the first assembly and has a tangent angle α of about 270 degrees. Loop 203 is the first loop intersecting the central axis 20 and therefore defines the first disk 40. Loop 203 is positioned approximately perpendicular through the central axis 20 and therefore has an intersecting angle μ of about 90 degrees and a rotational angle β of about zero degrees. Loop 204 is formed by a second assembly and has a tangent angle α of about 135 degrees. Loop 205 defines the second disk and has an intersecting angle μ of about 90 degrees and a rotational angle β of about zero degrees. Loop 206 defines the third assembly and has a tangent angle α of about 225 degrees. Loop 207 is also positioned on the third assembly and has a tangent angle α of about 315 degrees. Loop 208 is an intersecting loop 102 and defines a third disk. Loop 208 intersects the central axis 20 at an angle nonperpendicular to the axis 20. Loop 208 has an intersecting angle of about 75 degrees read on the Z,Y plane. Furthermore, loop 208 can be described as being rotated about the X,Y plane, i.e. it has a rotational angle β of about 45 degrees. Loop 209, is positioned about a circumference 30 of the central axis 20 and therefore defines a forth assembly. Loop 209 has a tangent angle α of about 135 degrees. Loop 210 defines a forth disk and has an intersecting angle μ of about 345 degrees and a rotational angle β of about 45 degrees. Loop 211 defines a fifth assembly and has a tangent angle α of about 315 degrees. Finally, loop 212 is also formed by the fifth assembly and has a tangent angle α of about 225 degrees.

As apparent from the positional description of loops 204, 206, 207, 209, 211, and 212, the planes defined by these loops are approximately 45 degrees askew from the planes defined by loops 201 and 202. This is best explained by the fact that loop 201 defines the reference plane of the device. From a fabrication perspective, the offset is best illustrated in FIG. 3. The mandrel 50 is configured such that the assembly 30b is oriented 45 degrees askew to the assemblies 30a and 30c-e.

Example 2

With reference to FIGS. 7A-7D, device 300 includes loops 301-312. The orientation of each loop with reference to the reference frame described above is provided in TABLE 2.

TABLE 2

DESCRIPTION OF EXAMPLE 2.

| Loop No. | Loop Diameter (mm) | Assembly No. | Tangent Angle (α) (Deg.) | Disk No. | Intersecting Angle (μ) (Deg) | Rotational Angle (β) (Deg) |
|---|---|---|---|---|---|---|
| 301 | -2 | 1 | 0 | | | |
| 302 | -1 | 1 | 90 | | | |
| 303 | Nominal | | | 1 | 90 | 0 |
| 304 | -1 | 2 | 315 | | | |
| 305 | -1 | 2 | 225 | | | |
| 306 | Nominal | | | 4 | 90 | 0 |
| 307 | Nominal | 3 | 90 | | | |
| 308 | Nominal | | | 3 | 90 | 0 |
| 309 | -1 | 4 | 315 | | | |
| 310 | -1 | 4 | 225 | | | |
| 311 | Nominal | | | 4 | 90 | 0 |
| 312 | -2 | 5 | 90 | | | |

Example 3

With reference to FIGS. 8A-8D, device 400 includes loops 401-412. The orientation of each loop with reference to the reference frame described above is provided in TABLE 3.

TABLE 3

DESCRIPTION OF EXAMPLE 3

| Loop No. | Loop Diameter (mm) | Assembly No. | Tangent Angle (α) (Deg.) | Disk No. | Intersecting Angle (μ) (Deg) | Rotational Angle (β) (Deg) |
|---|---|---|---|---|---|---|
| 401 | -2 | 1 | 0 | | | |
| 402 | -1 | 1 | 90 | | | |
| 403 | Nominal | | | 1 | 90 | |
| 404 | -1 | 2 | 315 | | | |
| 405 | Nominal | | | 2 | 90 | 0 |
| 406 | -1 | 3 | 90 | | | |
| 407 | -1 | 3 | 180 | | | |
| 408 | Nominal | | | 3 | 345 | 45 |
| 409 | -1 | 4 | 315 | | | |
| 410 | -Nominal | | | 4 | 90 | 0 |
| 411 | -1 | 5 | 180 | | | |
| 412 | -2 | 5 | 90 | | | |

Example 4

With reference to FIG. 9A-9D, device 500 includes loops 501-512. The orientation of each loop with reference to the reference frame described above is provided in TABLE 4.

TABLE 4

DESCRIPTION OF EXAMPLE 4

| Loop No. | Loop Diameter (mm) | Assembly No. | Tangent Angle (α) (Deg.) | Disk No. | Intersecting Angle (μ) (Deg) | Rotational Angle (β) (Deg) |
|---|---|---|---|---|---|---|
| 501 | -2 | 1 | 0 | | | |
| 502 | -1 | 1 | 90 | | | |
| 503 | Nominal | | | 1 | 90 | 0 |
| 504 | -1 | 2 | 315 | | | |
| 505 | Nominal | | | 2 | 90 | 0 |
| 506 | -1 | 3 | 90 | | | |
| 507 | -1 | 3 | 180 | | | |
| 508 | -1/2 | | | 3 | 75 | 270 |
| 509 | -1 | 4 | 0 | | | |
| 510 | -1/2 | | | 4 | 345 | 270 |
| 511 | -1 | 5 | 180 | | | |
| 512 | -2 | 5 | 90 | | | |

Example 5

Figure 11:
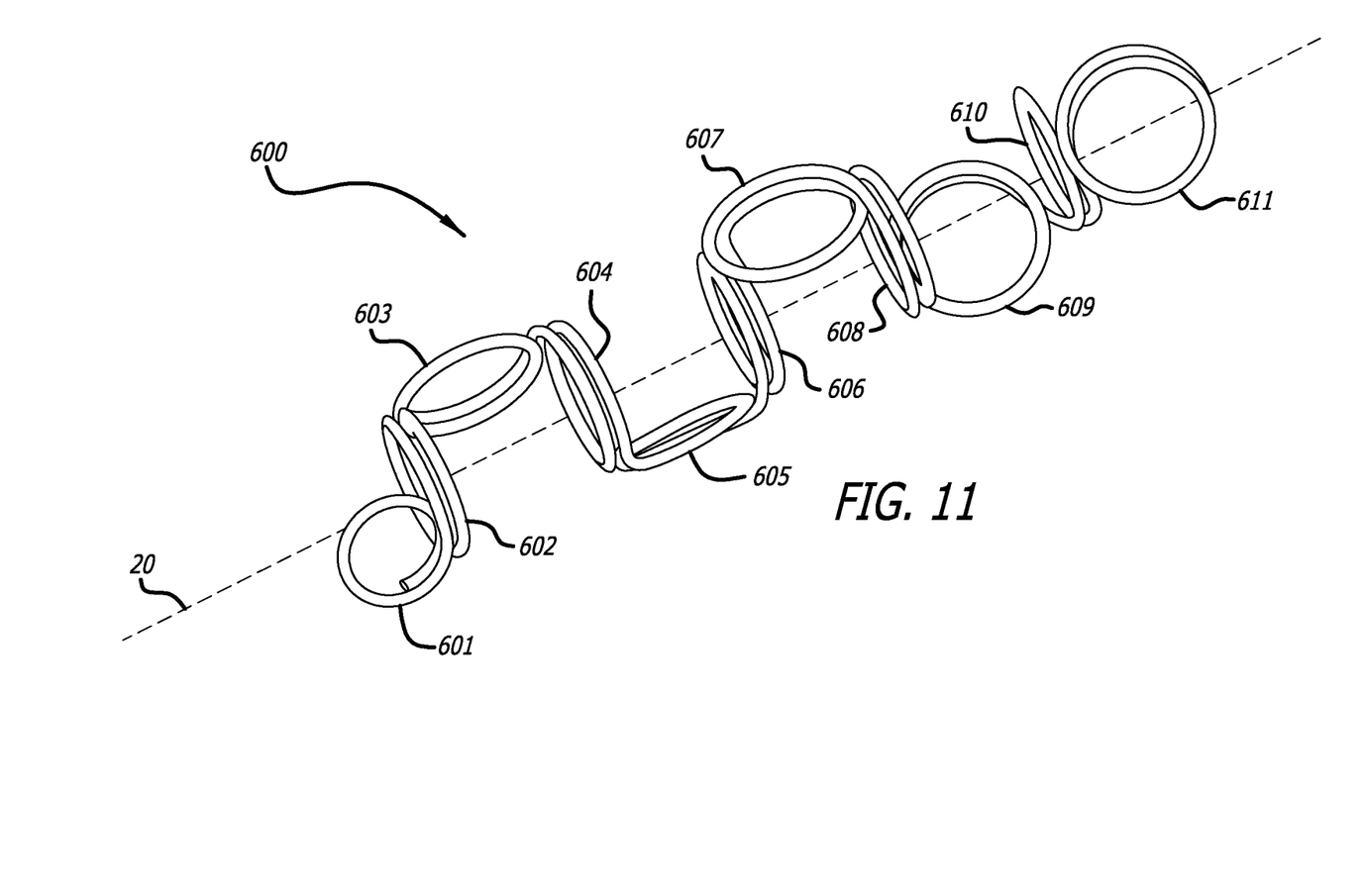
FIG. 11 is a perspective view of an embodiment of a device according to the present invention.

With reference to FIG. 11, device 600 includes loops 601-611. As apparent from FIG. 11, loops 601-611 alternate between tangential loops 100 and intersecting loops 102. Stated alternatively, each loop 100 is interposed between two loops 102 and each loop 102 is interposed between two loops 100. As also apparent from FIG. 11, each adjacent pair of loops reside in planes that are approximately perpendicular to one another, i.e. adjacent pairs of loops reside in planes that intersect to form an angle of approximately 90 degrees.

In order to deliver the device 10 to the target, such as an aneurysm, the proximal end of the microcoil 14 of device 10 is attached to the distal end of an elongate delivery device, such as a guidewire or microcatheter (not shown). The attachment may be by any of a number of ways known in the art, as exemplified by the following U.S. patents, the disclosures of which are expressly incorporated herein by reference: U.S. Pat. No. 5,108,407 to Geremia et al.; U.S. Pat. No. 5,122,136 to Guglielmi et al.; U.S. Pat. No. 5,234,437 to Sepetka; U.S. Pat. No. 5,261,916 to Engelson; U.S. Pat. No. 5,304,195 to Twyford, Jr. et al.; U.S. Pat. No. 5,312,415 to Palermo; U.S. Pat. No. 5,423,829 to Pham et al.; U.S. Pat. No. 5,522,836 to Palermo; U.S. Pat. No. 5,645,564 to Northrup et al.; U.S. Pat. No. 5,725,546 to Samson; U.S. Pat. No. 5,800,453 to Gia; U.S. Pat. No. 5,814,062 to Sepetka et al.; U.S. Pat. No. 5,911,737 to Lee et al.; U.S. Pat. No. 5,989,242 to Saadat et al.; U.S. Pat. No. 6,022,369 to Jacobsen et al.; U.S. Pat. No. 6,063,100 to Diaz et al.; U.S. Pat. No. 6,068,644 to Lulo et al.; and U.S. Pat. No. 6,102,933 to Lee et al.

A method for treating a vascular target with the device 10 may include visualizing the target vascular site by means well-known in the art. The target vascular site may be, for example, an aneurysm branching off a parent artery. Such an aneurysm may have a dome connected to the branch artery by a neck. A catheter is passed intravascularly until it enters the dome of the aneurysm via the neck. The device 10 is passed through the catheter with the assistance of the guidewire or microcatheter until a distal end of the device 10 enters the dome of the aneurysm.

As the device 10 enters the aneurysm, it attempts to assume its secondary configuration. Because the microcoil, in its secondary configuration, is larger than the aneurysm, however, it is constrained into a deployed configuration in which it tends to line the periphery of the aneurysm. In this deployed configuration, the microcoil is in an energy state that is substantially higher than its minimum energy state. Thus, when the device is deployed inside a vascular site such as an aneurysm, the confinement of the device within the site causes the device to assume a three-dimensional configuration that has a higher energy state than the minimum energy state. Because the minimum energy state of the device is larger (in at least one dimension) than the space in which it is deployed, the deployed device is constrained by its intimate contact with the walls of the aneurysm from returning to its minimum energy state configuration. Therefore, the device still engages the surrounding aneurysm wall surface, thereby minimizing shifting or tumbling due to blood flow dynamics. Furthermore, the minimum energy state secondary configuration (to which the device attempts to revert) is not one that is conducive to "coin stacking", thereby minimizing the degree of compaction that is experienced.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A vaso-occlusive device comprising:
   a microcoil having a primary configuration and a secondary configuration;
   said microcoil in said secondary configuration having a central axis and a plurality of closed loops connected in series along said central axis;
   each of said plurality of closed loops residing in either an intersecting plane defined by a plane that intersects said central axis or in a tangential plane defined by a plane that is tangent to a circumference around said central axis;

wherein somewhere along said microcoil in said secondary configuration a successively formed series of four loops of said plurality of closed loops comprises two of said plurality of closed loops each residing in an intersecting plane longitudinally separated from one another along said central axis by only one of said plurality of closed loops residing in a tangential plane.

2. The device of claim 1 wherein substantially all of the plurality of closed loops are tangentially-interconnected.

3. The device of claim 1 wherein at least two of said plurality of closed loops residing in intersecting planes reside in planes that intersect the central axis at an angle other than 90 degrees.

4. The device of claim 1 wherein at least two of said plurality of closed loops residing in intersecting planes reside in planes that intersect the central axis at an angle of 75 degrees.

5. The device of claim 1 wherein the plurality of closed loops comprises:
   a first loop residing in a first plane;
   a second loop residing in a second plane that forms an angle of approximately 90 degrees with the first plane; and
   a third loop residing in a third plane that forms an angle of approximately 90 degrees with the first plane and the second plane.

6. The device of claim 1 wherein substantially the entire length of the microcoil forms curves.

7. The device of claim 1 wherein the planes in which each pair of adjacent loops reside form a non-zero degree angle.

8. The device of claim 1 wherein each of the loops has a diameter and a variability between the diameters of each of the loops is less than 4 millimeters.

9. A vaso-occlusive device comprising:
   a microcoil having a secondary configuration that contains successively formed loops in a series of planes along a central axis, each loop in said series formed in its entirety prior to formation of a succeeding loop in said series;
   said series of planes comprising either intersecting planes or tangent planes;
   wherein said intersecting planes intersect said central axis of said secondary configuration;
   wherein said tangent planes are tangent to a circumference of said central axis of said secondary configuration; and
   wherein each loop residing in a tangential plane is separated by a closed loop residing in one of said intersecting planes from a next longitudinally occurring loop residing in a tangential plane, in said secondary configuration.

10. The device of claim 9 wherein at least one of said plurality of intersecting planes intersects said central axis at an angle other than 90 degrees.

11. The device of claim 9 wherein at least one of said plurality of intersecting planes intersects said central axis at an angle of 75 degrees.

12. The device of claim 9 wherein an entire length of the structure forms curves.

13. The device of claim 9 wherein said structure in at least two of said loops in said series of planes defines a diameter and a variability between the diameters is less than 4 millimeters.

14. The device of claim 9 wherein said series of planes along said central axis comprises:
   a first plane;
   a second plane; and
   a third plane;
   wherein said first plane forms an angle of approximately 90 degrees with said second plane; and
   a third plane forms an angle of approximately 90 degrees with the first plane and the second plane.

15. A vaso-occlusive device comprising:
   a microcoil forming a structure having a secondary configuration comprising a series of interconnected loops, each loop circumscribing a planar area prior to formation of a succeeding loop;
   wherein the planar areas of sequentially formed loops in said series are arranged as follows:
   a first planar area;
   a second planar area substantially meets and forms an angle of approximately 90 degrees with the first planar area;
   a third planar area substantially meets first and second planar areas to form angles of approximately 90 degrees with the first and second planar areas;
   a fourth planar area; and,
   a fifth planar area;
   wherein the fourth planar area substantially meets third and fifth planar areas to form angles exclusively with the third and fifth planar areas.

16. The device of claim 15 wherein at least one of the loops is closed.

17. The device of claim 15 wherein at least one pair of adjacent loops in said series are tangentially-interconnected.

18. The device of claim 15 wherein the fourth planar area is parallel with at least one other planar area circumscribed by a loop in the series.

19. The device of claim 15 wherein at least two loops in said series circumscribe planar areas that intersect a central axis formed through the structure in the secondary configuration.

20. The device of claim 1 wherein somewhere along said microcoil in said relaxed state at least two of said plurality of loops are each formed by winding the microcoil 1.25 rotations.

21. The device of claim 9 wherein at least two of the loops are each formed by winding the microcoil 1.25 rotations.

22. The device of claim 21 wherein the at least two of the loops are the second and third loops of the device.

23. The device of claim 15 wherein the series of interconnected loops comprises at least two loops that are each formed by winding the microcoil approximately 1.25 rotations.

24. The device of claim 23 wherein the at least two successive loops are the second and third loops of the device.

* * * * *